United States Patent [19]

Stabile

[11] 4,046,511

[45] Sept. 6, 1977

[54] PIPETTOR APPARATUS

[75] Inventor: James Stabile, Scarsdale, N.Y.

[73] Assignee: Union Carbide Corporation, New York, N.Y.

[21] Appl. No.: 587,202

[22] Filed: June 16, 1975

[51] Int. Cl.² .................. G01N 33/16; G01N 1/14
[52] U.S. Cl. ................... 23/259; 23/253 R; 73/425.4 P
[58] Field of Search ............ 23/253 R, 259; 141/130; 73/425.4 P

[56] References Cited

U.S. PATENT DOCUMENTS

| | | | |
|---|---|---|---|
| 3,594,129 | 7/1971 | Jones | 23/259 X |
| 3,679,367 | 7/1972 | Negersmith et al. | 23/259 |
| 3,728,079 | 4/1973 | Moran | 23/259 X |
| 3,801,283 | 2/1974 | Shapiro et al. | 23/259 |

Primary Examiner—R.E. Serwin
Attorney, Agent, or Firm—Frederick J. McCarthy, Jr.

[57] ABSTRACT

Apparatus for automatically and rapidly transferring precise, accurate multiple quantities of samples, such as blood serum, reagent to a rotatable disc of a centrifugal analyzer.

3 Claims, 28 Drawing Figures

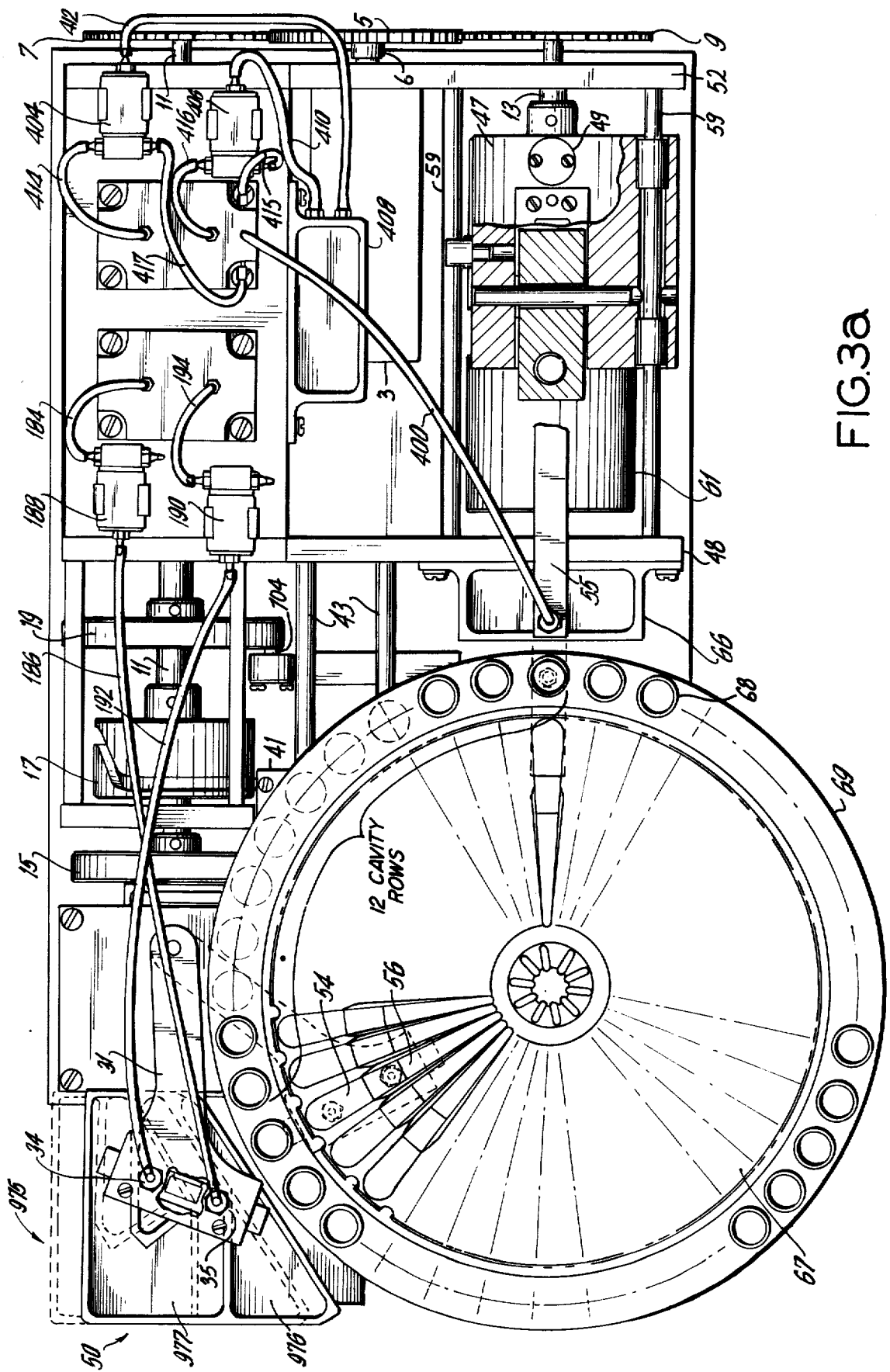

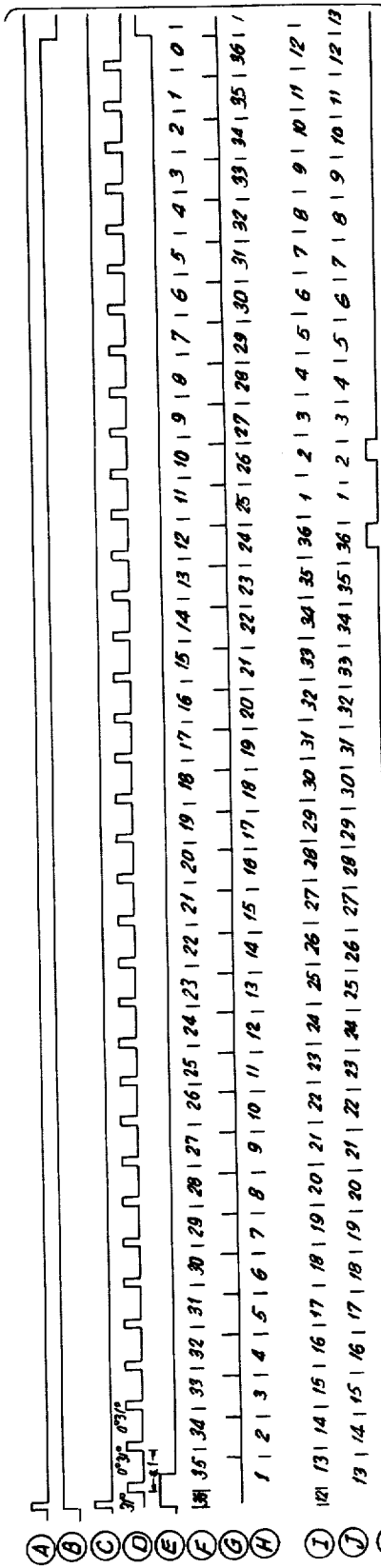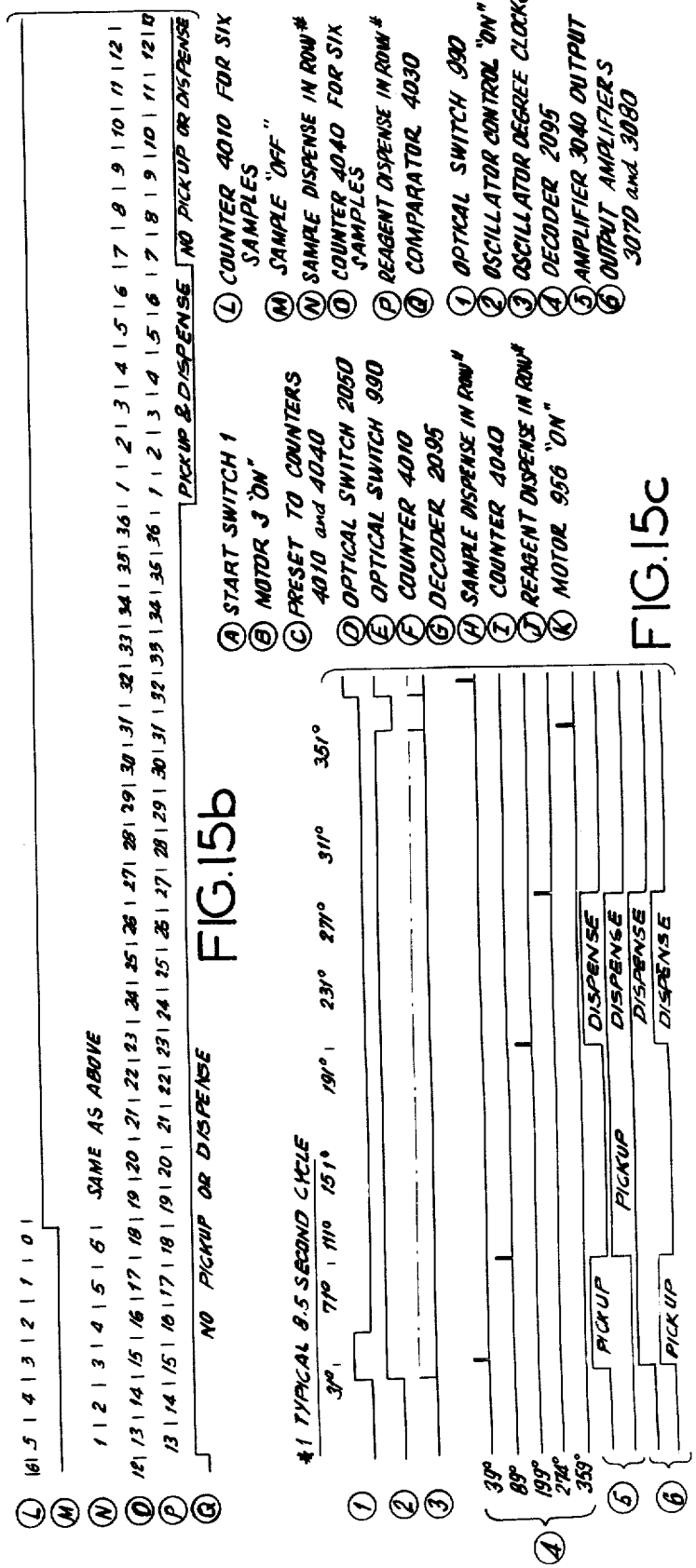
FIG.15a
FIG.15b
FIG.15c

PIPETTOR APPARATUS

This invention relates to an apparatus for automatically and rapidly transferring accurate and precise multiple quantities of samples (e.g. such as blood serum specimens) and reagent to the rotatable transfer disc of a centrifugal analyzer of the type disclosed in U.S. patent application Ser. No. 468,649, filed May 10, 1974 in the name of S. Shapiro and G. Ertingshausen and issued as U.S. Pat. No. 3,953,172.

The centrifugal analyzer of the type disclosed in the above-noted patent application, the disclosure of which is incorporated herein by reference, utilizes a centrifugal field to transfer sample and reagent from the radially aligned cavities of a rotatable disc to separating and analyzing devices. It is important that the rotatable disc be rapidly and accurately loaded with precise quantities of liquid sample and reagents, including radiolabelled liquids such as $I_{125}$ solutions.

It is therefore an object of the present invention to provide an apparatus for rapidly transferring accurate multiple quantities of serum and reagent to the rotatable disc of a centrifugal analyzer.

Other objects will be apparent from the following description and claims taken in conjunction with the drawing wherein.

FIG. 3(a) is a plan view of the apparatus of FIG. 2.

FIGS. 9(a) through 9(e) shows cams which form a part of the present invention and act to control the movement of the reagent arm, pumps and indexing of the apparatus of the present invention; diagrams for a revolution of the perspective cams are also shown.

Figure 10A:
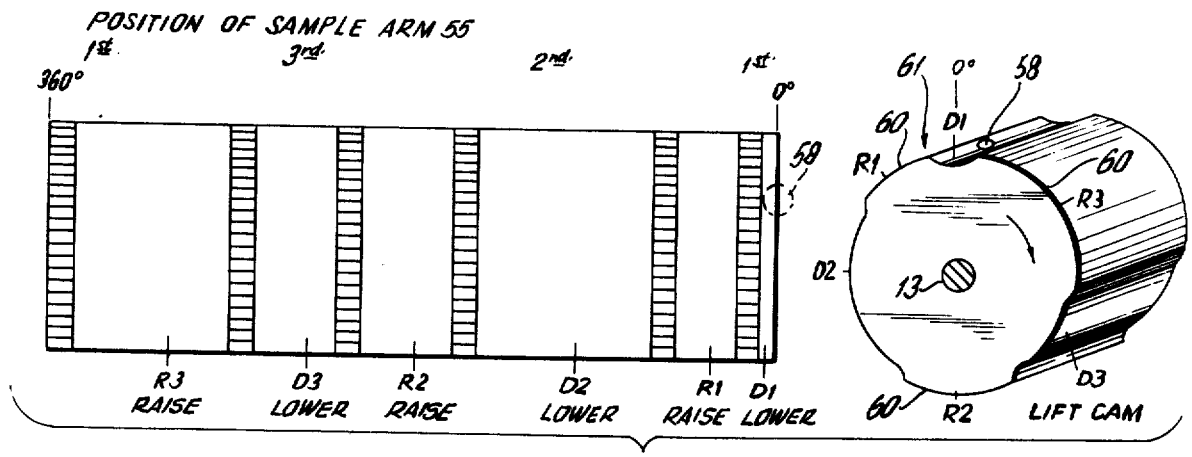
Figure 10B:
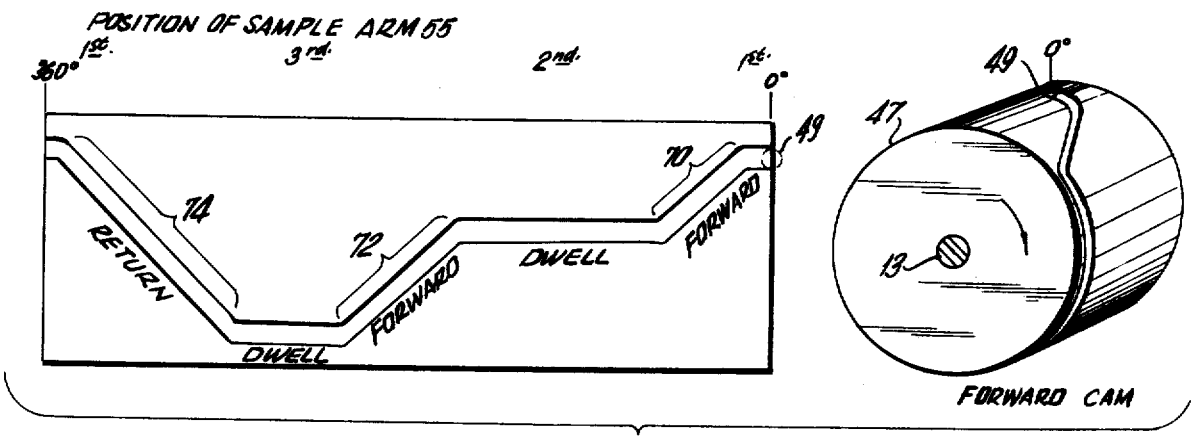

FIGS. 10(a) and 10(b) show cams which form a part of the present invention and act to control the movement of the sample arm of the apparatus of the present invention; diagrams for a revolution of the respective cams are also shown.

Figure 11:
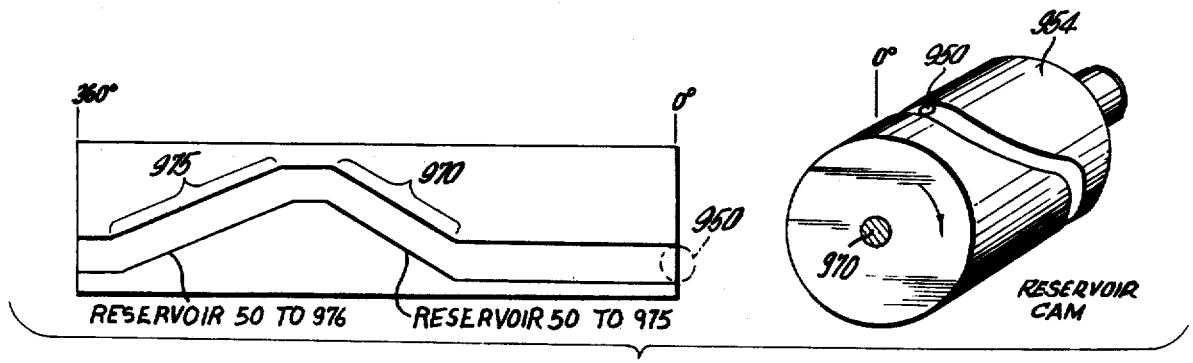

FIG. 11 shows a cam which forms a part of the present invention and acts to control the position of the reagent reservoir with respect to the reagent probe arm; a diagram for a revolution of the cam is also shown.

Figure 12A:
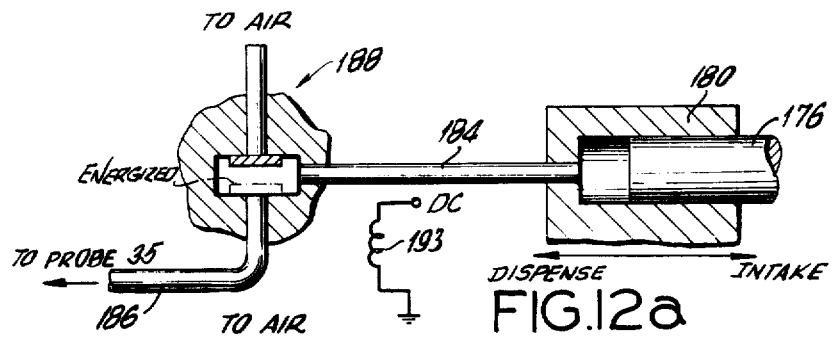
Figure 12B:
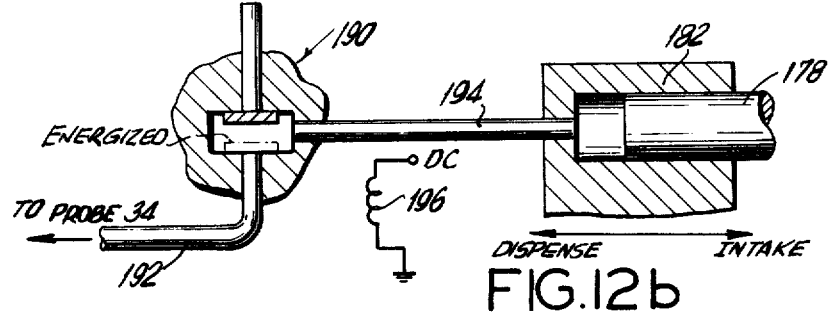

FIGS. 12(a) and 12(b) show diagrams illustrating the operation of syringe pumps of the present invention which pick up and dispense reagent.

Figure 13:
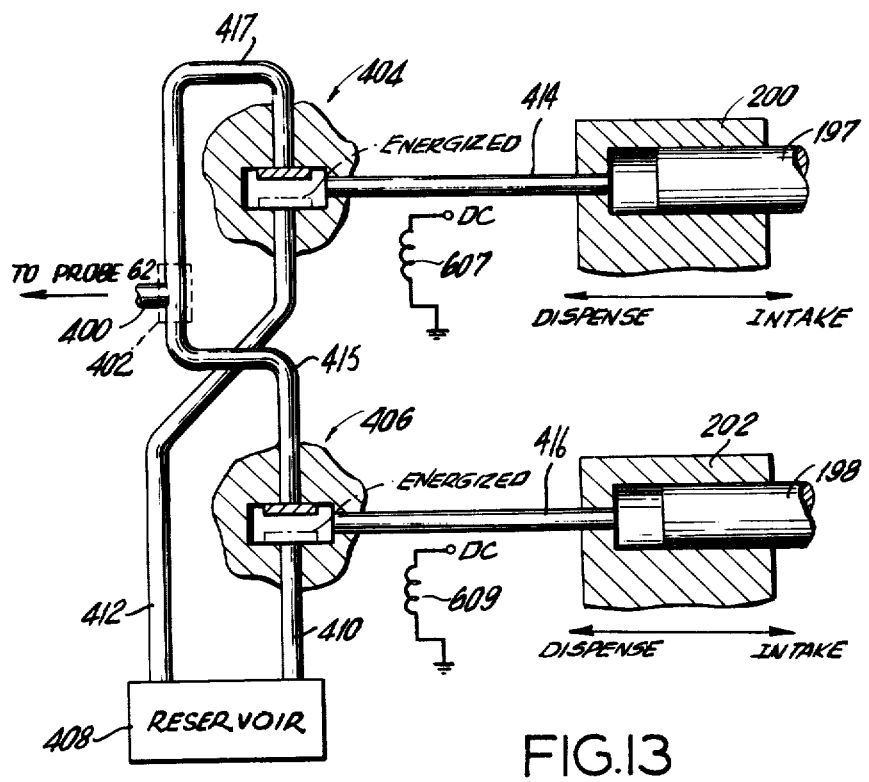
Figure 13A:
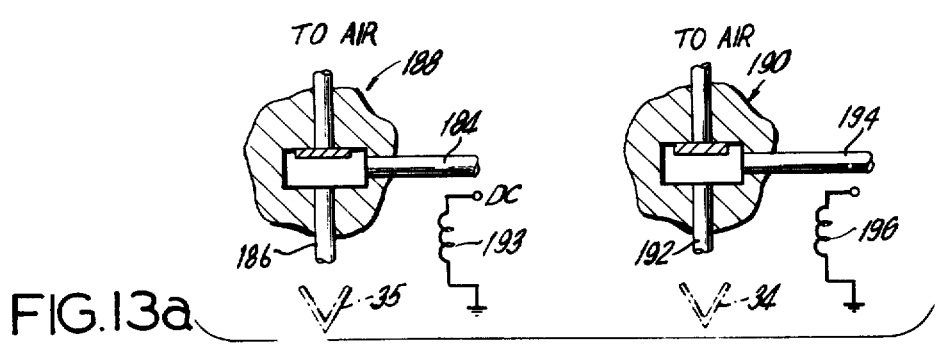

FIGS. 13 and 13(a) show diagrams illustrating the operation of syringe pumps of the present invention which pick up and dispense sample and diluent.

Figure 14:
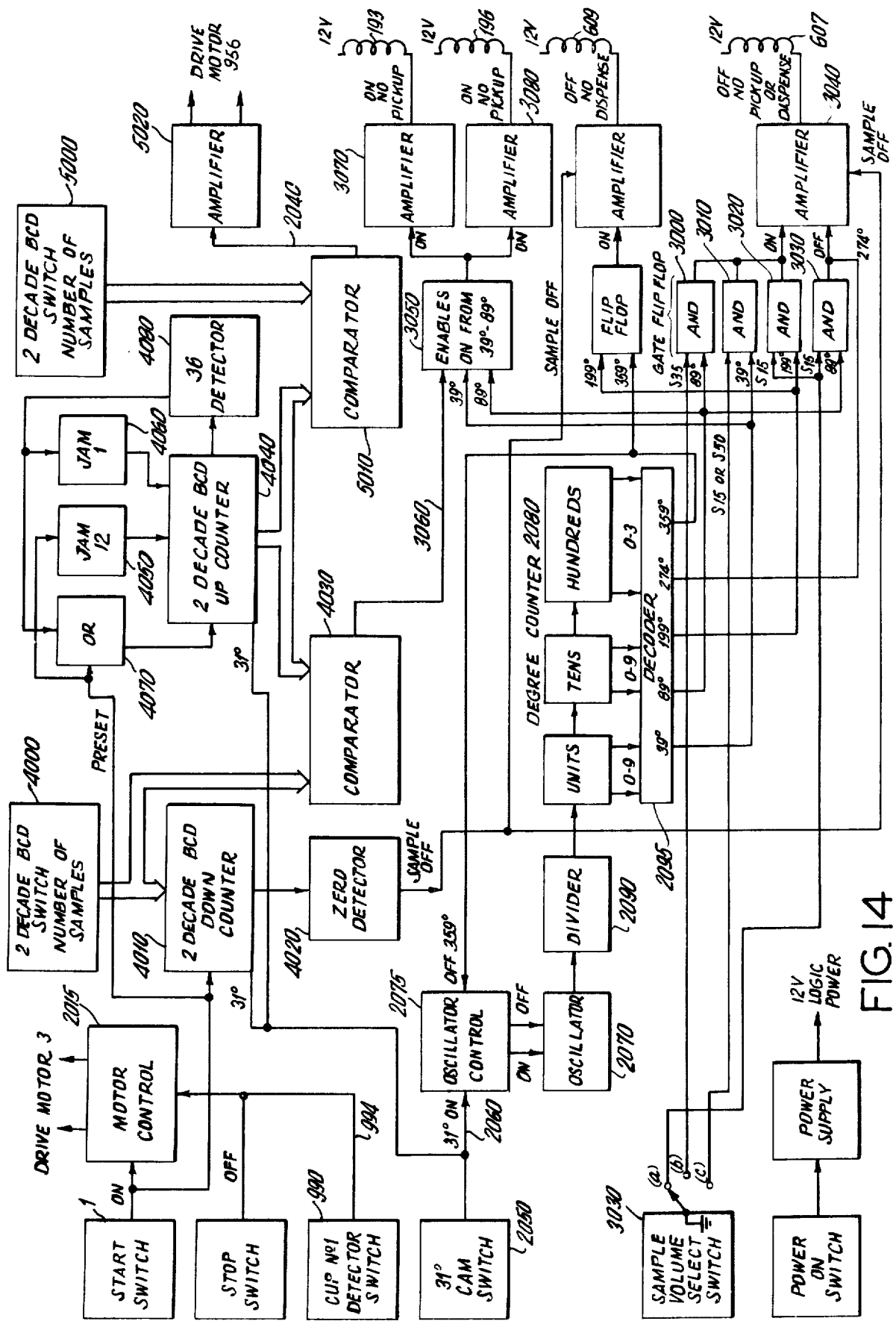

FIG. 14 is an electrical schematic showing an arrangement form providing electrical signals used in the operation of the apparatus of the present invention.

FIGS. 15(a), (b) and (c) are time diagrams relating the electrical signals of FIG. 14.

Figure 1:
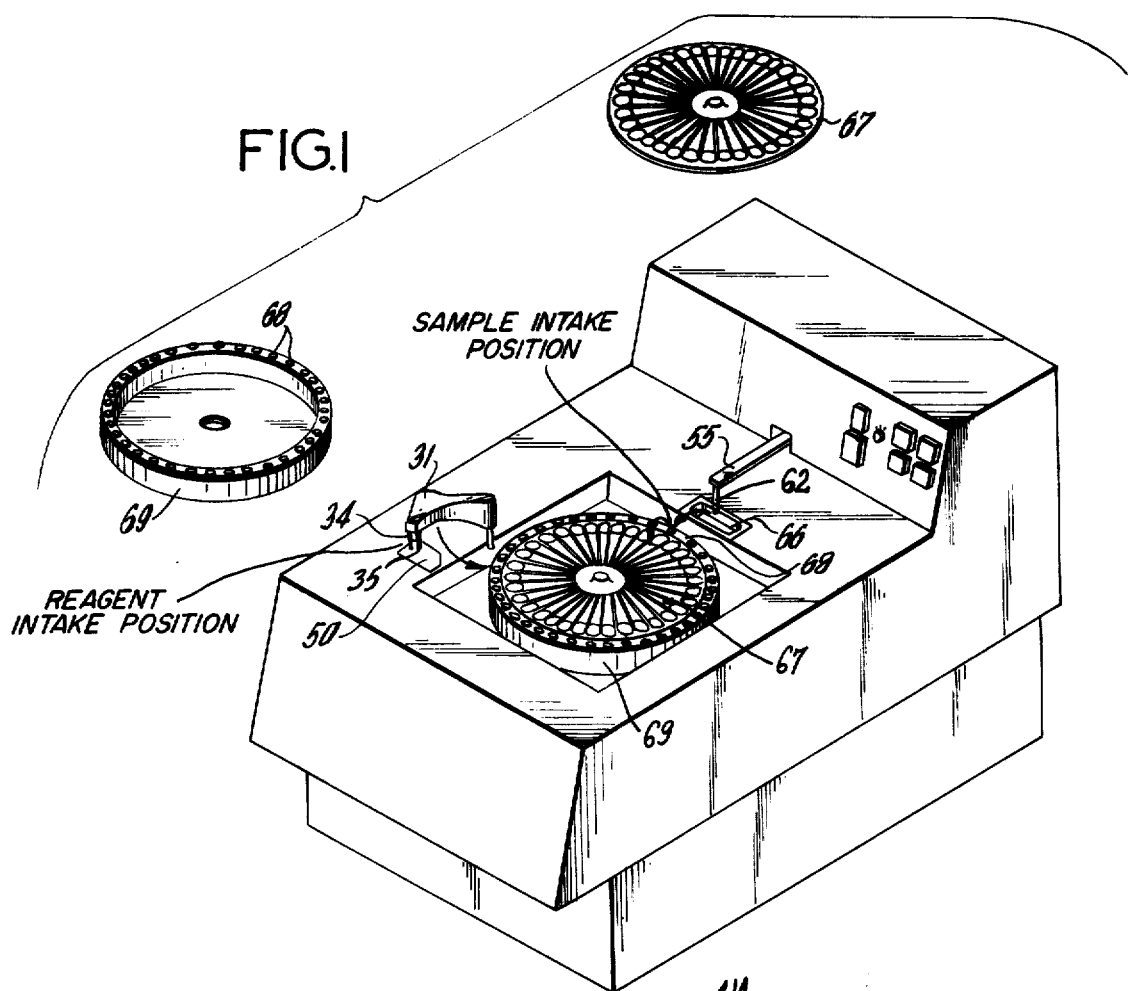
FIG. 1 is a perspective view of a pipettor apparatus in accordance with the present invention showing the general arrangement of elements directly involved in the loading of a multicavity disc with reagents and sample.

With reference to FIG. 1, the unit shown has a removeable multicavity transfer disc 67 and sample ring 69 and sample cups 68 in place. The transfer disc 67, sample ring 69 and cups 68 are more fully illustrated in FIGS. 4(a), 4(b) and 4(c). Upon actuation of appropriate panel switches a precise amount of liquid reagent is drawn into the reagent probes 34 and 35 from the reagent containing reservoir 50 and the reagent arm 31 is raised upward and then swung over to a reagent dispense position and lowered to extend the reagent probes 34 and 35 into the appropriate cavities of a radial row in the multicavity transfer disc 67. With the reagent probes 34 and 35 so located, a precise amount of reagent is dispensed into the underlying cavities and the reagent arm 31 is raised and moved back and lowered into the initial sample intake position. Concurrently, the sample arm 55 and sample probe 62 is moved from wash liquid reservoir 66 to the sample intake position where the sample probe 62 is immersed in the liquid contents of a sample cup 68X and a precise amount of sample is drawn into the sample probe 62 which is then moved to the sample dispense position where the sample probe 62 extends into an appropriate cavity of a radial row in the multicavity transfer disc 67. With the sample probe 62 so located a precise amount of sample is dispensed into the underlying cavity and the sample arm 55 is raised and moved back to its starting position with the sample probe immersed in liquid in the wash reservoir. The same intake-dispense cycle is repeated for each cavity row to be filled, the multicavity disc 67 and sample ring 69 being advanced after each intake-dispense cycle is completed to bring the next cavity radial row into position. As can be seen, sample and reagents are not dispensed into the same row of cavities during a given intake-dispense cycle. Consequently, in situations where less than all of the cavity rows are selected to receive reagent and sample, the dispensing of reagents and sample is controlled by the apparatus of the present invention so that only the selected cavities receive reagents.

Figure 3B:
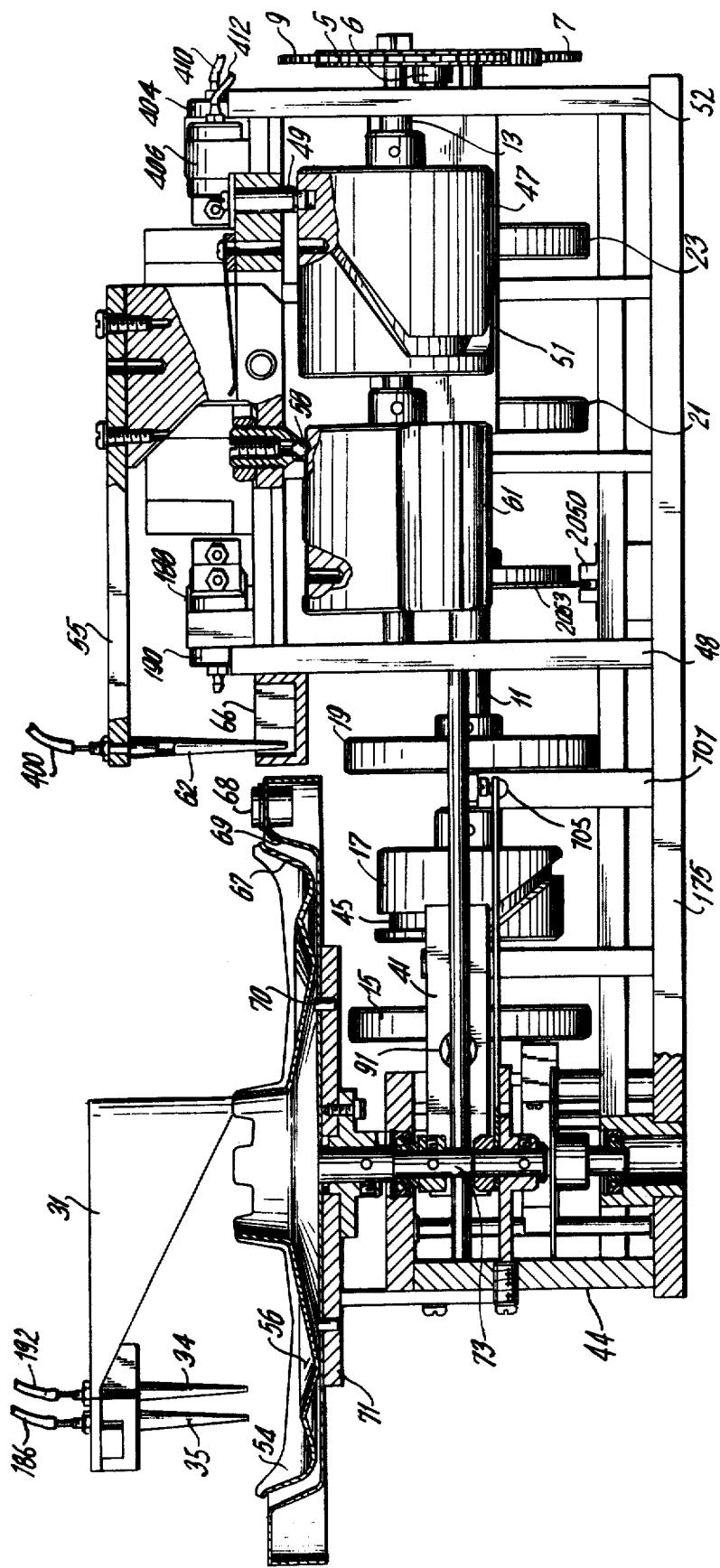
FIG. 3(b) is an elevational view of the apparatus of FIG. 2.

With reference to FIG. 3(a), the dispensing of sample and reagents for the first intake-dispense cycle using a 36 row multicavity disc is illustrated where the respective loading positions for sample and reagents are offset by 12 cavity rows.

The offsetting of the dispensing positions for reagent and sample, e.g. being located in different quadrants, enables an efficient and compact mechanical drive arrangement as hereinafter described and, together with the controlled motion of the probe supporting arms, minimizes the likelihood of accidental premature mixing of reagents and sample.

Figure 4A:
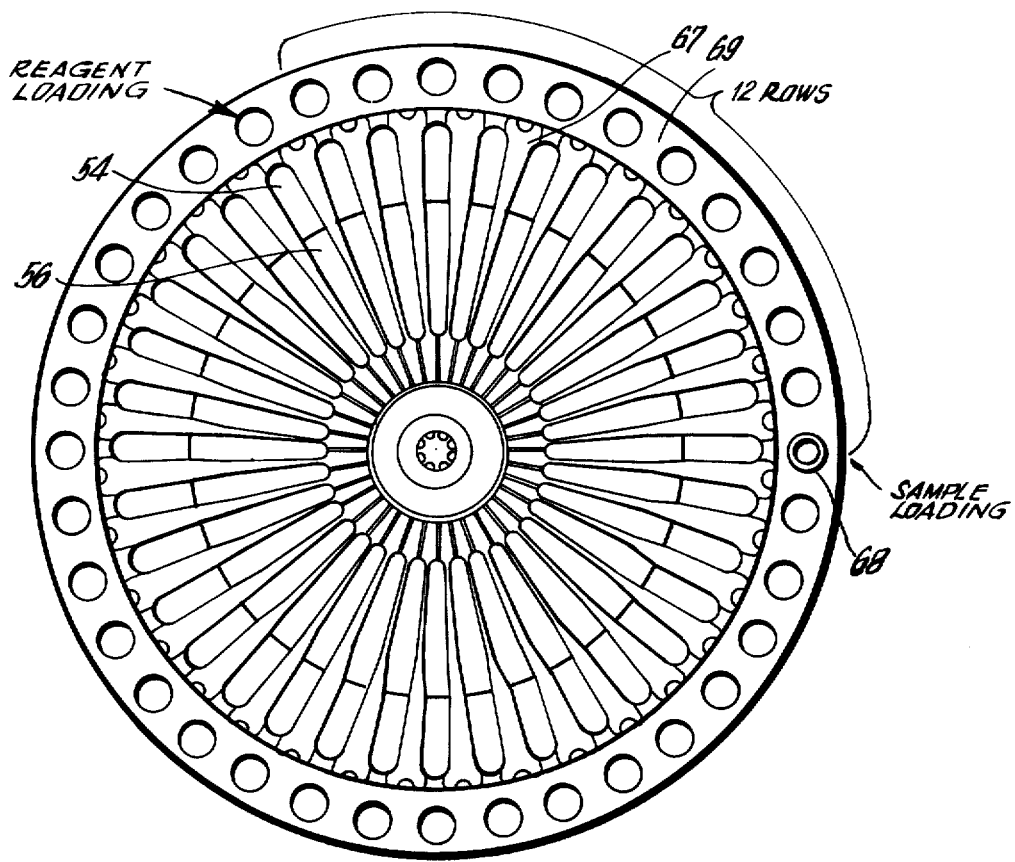
FIG. 4(a) is a plan view of a multicavity disc and sample ring of the type used with the apparatus of the present invention.
Figure 4B:
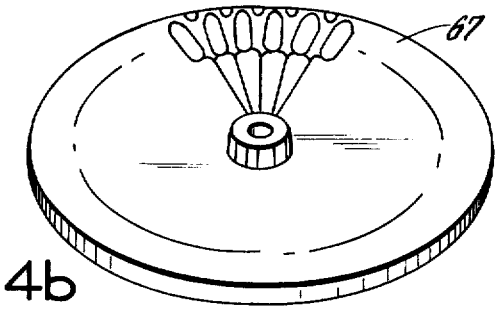
FIG. 4(b) shows the multicavity disc of FIG. 4(a) separated from the sample ring shown in FIG. 4(a).

The pipettor apparatus of the present invention can be used to load multicavity transfer discs of the type shown in FIGS. 4(a) and 4(b) with the liquid reagents and samples regularly used in analyses performed by centrifugal analyzers of the type hereinbefore described. By way of a specific example, the sample can be blood serum and the reagents can be antibody and an isotope such as $I_{125}$, the transfer disc upon loading being in condition for use in the analyzer described in the above-noted U.S. patent application Ser. No. 468,649.

Figure 2:
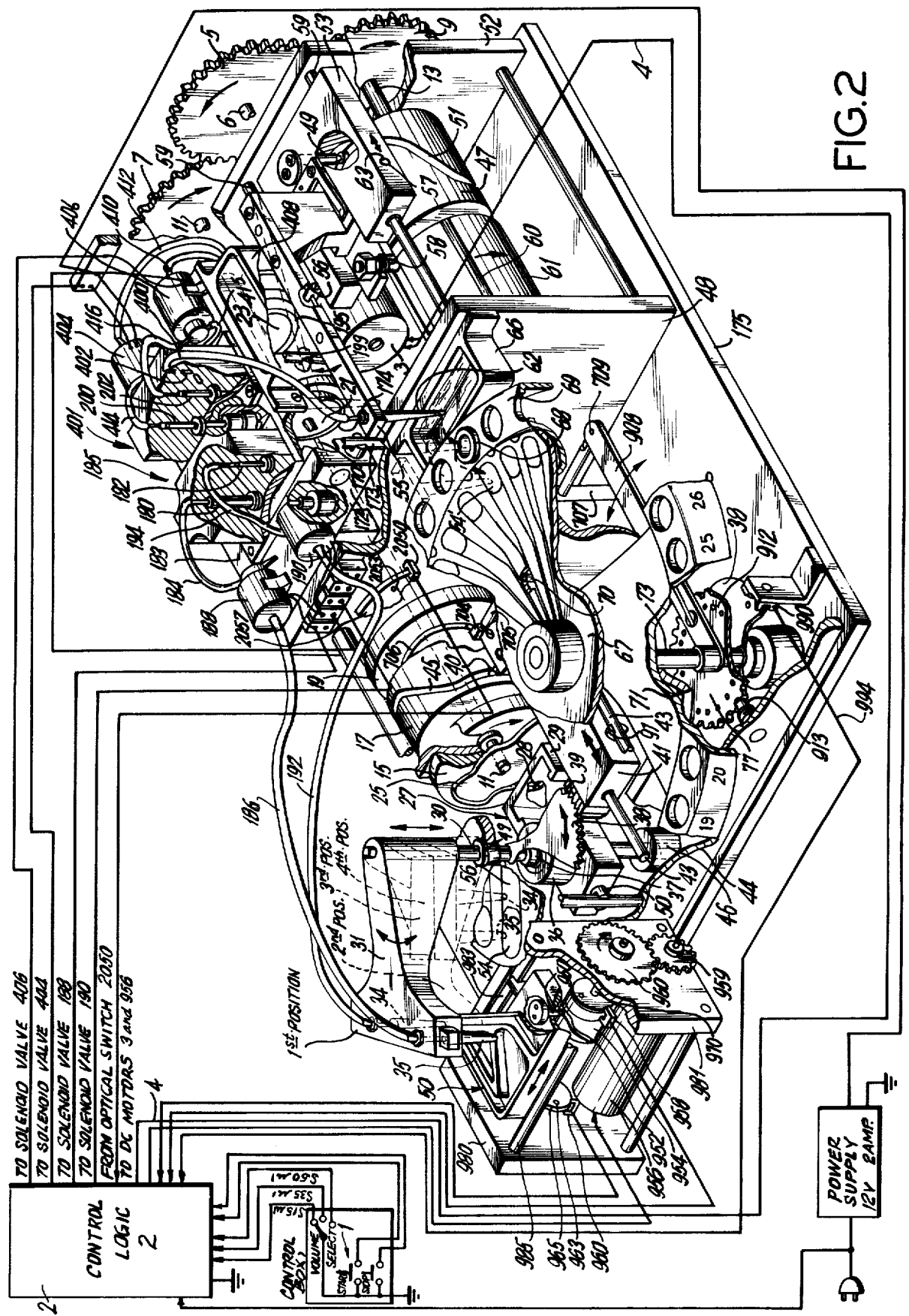
FIG. 2 is a perspective view of a pipettor apparatus of the present invention showing the mechanical elements of the apparatus and the electrical input and output connections involved in the operation of the apparatus.
Figure 4C:
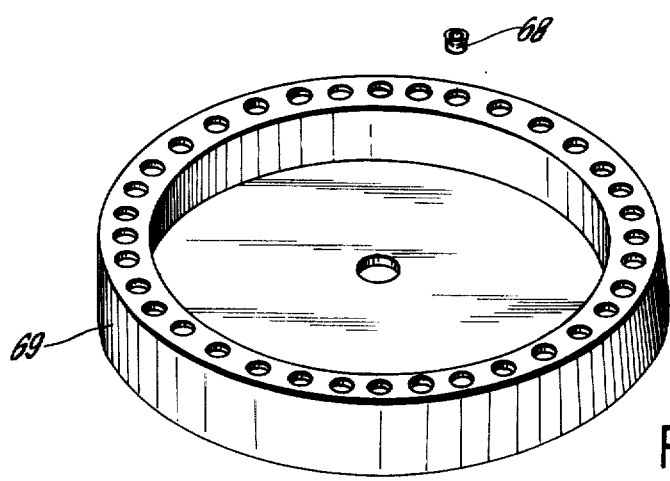
FIG. 4(c) shows the sample ring of FIG. 4(a) and a sample cup of the type used in conjunction with the sample ring.

With reference to FIG. 2, a multicavity transfer disc 67 and sample ring 69 of the type shown in FIGS. 4(a), 4(b) and 4(c) are engaged by pin arrangement 70 to support plate 71 which is fixed to shaft 73. Reagent arm 31 and sample arm 55 are initially positioned in a "first position" as shown. With electrical power applied to the apparatus the cams arranged on shafts 11 and 13 coact to move arms 31 and 55 in the concurrent motions afore-described and cause reagents and sample to be picked up and dispensed in the appropriate cavities of multicavity disc 67. After each intake-dispense cycle, disc 67 is advanced, by rotation of shaft 73 to bring another row of cavities into position.

In operation, with reference to FIG. 2, switch 1 is closed and a.c. line power is applied to drive motor 3 by way of wire leads 4 which are connected to Control Logic circuitry 2 as herein after described. Drive motor 3 is mechanically engaged to gear 5 by way of drive motor shaft 6 and rotates therewith in the direction indicated. Gear 5 engages gears 7 and 9 which rotate in the directions indicated and are fixedly coupled to parallel cam shafts 11 and 13 respectively. Mounted and fixed on shaft 11 are five cams 15, 17, 19, 21 and 23 more particularly described in connection with FIGS. 9(a) through (e). Cam 15 is a conventional box cam or positive motion cam having a groove 25 which engages a ball bearing follower assembly 27 comprising a follower 28 and a mounting block 29 through which shaft 30 passes and which supports thrust bearing 37 which is fixed to bushing 36 of block 29. Cam 15 is a "down-up" cam and functions to lower, raise and lower reagent arm 31.

Figure 7:
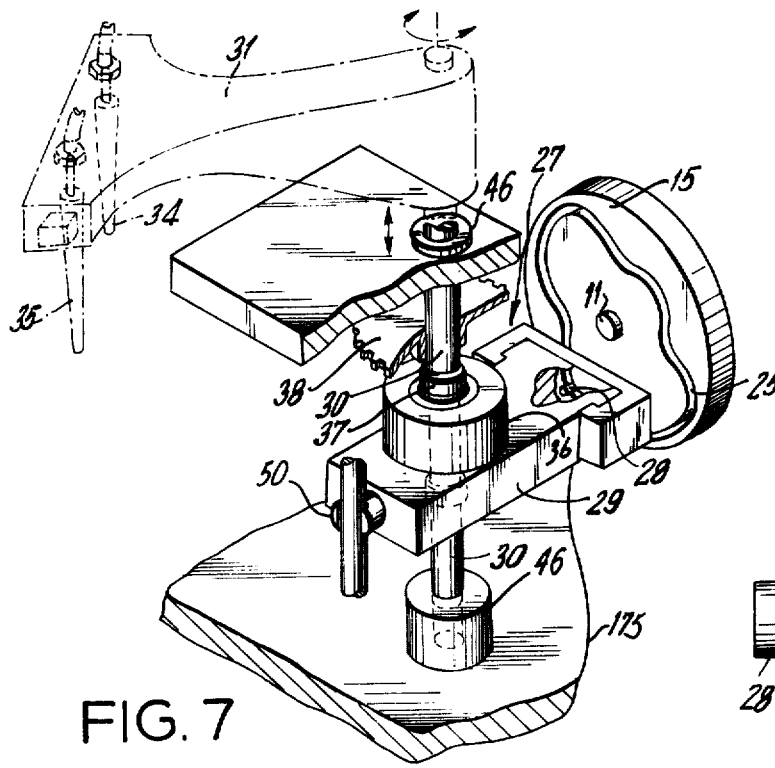
FIG. 7 shows a perspective view of the portion of the apparatus of the present invention which moves the reagent probe arm from an intake position to a dispense position and back to an intake position.
Figure 7A:
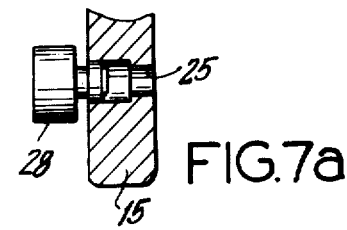
FIG. 7(a) is a sectional view of the cam-groove arrangement illustrated in FIG. 7.

With reference to FIG. 7 in conjunction with FIG. 2 shaft 30 is slidably engaged in bushing mounts 46 and is free to move vertically up and down with the movement of block 29 on which is supported thrust bearing 37. Shaft 30 is also free to rotate about its longitudinal axis upon rotation of gear 38 which is fixedly connected thereto. The vertical movement of shaft 30 which is controlled by cam 15 as previously described imparts vertical movement to reagent probe arm 31 which results in the lowering and raising of probes 34 and 35. Gear 38, fixedly attached to shaft 30 engages gear rack 39 which is mounted on slide 41. Slide 41 is free to move on shafts 43 which are supported by brackets 44 and 48 in conjunction with clevis 91. Slide 41 engages cylindrical cam 17 by way of follower 40 which engages groove 45 of cam 17. Rotation of cam 17, which is coordinated with cam 15, imparts reciprocal motion to slide 41 and rack 39, which causes gear 38 and shaft 30 to rotate back and forth as indicated. This motion of shaft 30 causes arm 31, and hence probes 34 and 35, to move back and forth between a position over reagent reservoir 50 and a position over outer and inner cavities 54 and 56, as shown also in FIG. 3(a). Cylindrical forward motion cam 47, fixedly mounted on shaft 13, is engaged to driven motor 3 by way of gear 9 as shown in FIG. 2, and functions to move sample probe arm 55 forward to a pickup and dispense position and back to its initial position. Slide 53 is mounted on rods 59 which are supported on brackets 48 and 52. Follower 49 of slide 53 is engaged with groove 51 of cam 47 and arm 55 is pivotally mounted on slide 53 by means of rod 63 as indicated at 57. Clevis 56 is supported by rod 59. Slide 53 moves back and forth upon rotation of cam 47 and sample arm 55 and sample probe 62 are thus similarly moved back and forth, sample probe 62 being moved back and forth from a position over wash reservoir 66 and a position over cavity 54'. As sample arm 55 is moved back and forth by coaction with cam 47, arm 55 is raised and lowered by the contact of follower 58 with the lobes 60 of cam 61 which is fixed to shaft 13 and rotates therewith.

The above described mechanical coaction is coordinated, as hereinafter described in conjunction with FIGS. 8, 9(a), to 9(e), 10(a) and 10(b) so as to move reagent probes 34 and 35, mounted on arm 31 in and out of separate compartments of reagent reservoir to to a position over disc cavities 54 and 56, while concurrently sample probe 62 on sample arm 55 moves from wash reservoir 66 to a sample cup 68 and to a position over an outer cavity 54' of multicavity disc 67.

With reference to FIGS. 10(a), 10(b), and 9(a) through 9(e), cams 61 and 47 of shaft 13, and cams 15 and 17 of shaft 11 are all shown in an indexed position, i.e. these are the relative positions of these cams on their respective shafts when reagent arm 31 and sample arm 55 are in the solid line "first" positions shown in FIG. 2. Upon rotation of drive motor 3 the cams rotate in the directions indicated and the movement of the followers engaged to the respective cams is illustrated in the associated cam diagrams. By way of example, with reference to FIGS. 10(a) and 10(b), with cams 47 and 61 of shaft 13 in their index positions, sample arm 55 is in the first position indicated in FIGS. 2 and 8. As the cams 47 and 61 are rotated by motor 3 on shaft 13, follower 58 of cam 61 is raised from location $D_1$ to $R_1$ of cam 61 as shown in FIG. 10(a) and sample arm 55 is raised to the "up position" shown in FIG. 8 and remains in a raised position while follower 49 of cam 47 is moved to the left in FIG. 8 along location 70 as shown in FIG. 10(b) to a position above sample cup 68. At this time follower 58 of cam 61 is lowered from location $R_1$ to location $D_2$ and arm 55 is in the second position shown in FIG. 8. Sample arm 55 dwells, i.e. remains in this position until follower 49 of cam 47 advances to the location 72 shown in FIG. 10(b). As cam follower 49 advances along location 72, arm 55 is moved forward toward the "third position" shown in FIG. 8; concurrently follower 58 of cam 61, as shown in FIG. 10(a), is raised at location $R_2$ and sample arm 55 remains raised until follower 58 is in contact with location $D_3$ in FIG. 10(a) when sample arm 55 is lowered to the third position shown in FIG. 8. Sample arm 55 is thereafter raised when follower 58 is contacted by cam 61 at location $R_3$ of FIG. 10(a) while concurrently follower 49 of cam 47 is returned at location 74 of FIG. 10(b), with sample arm 55, to the first position shown in FIG. 8.

Figure 9A:
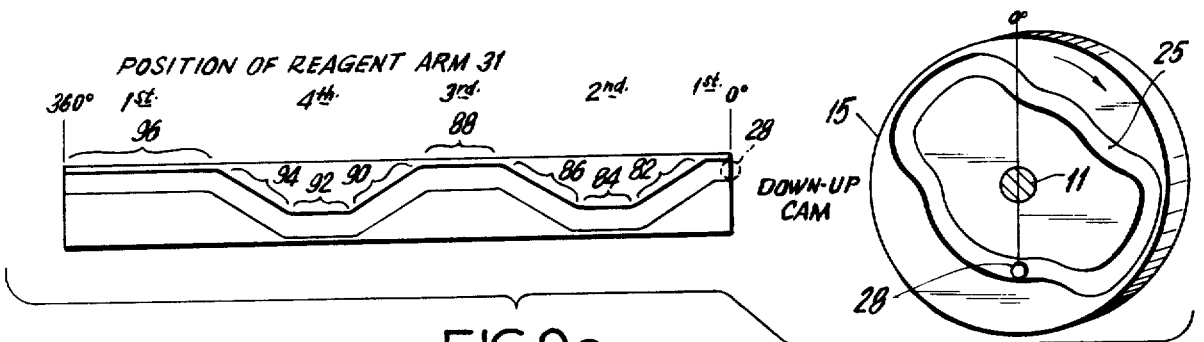
Figure 9B:
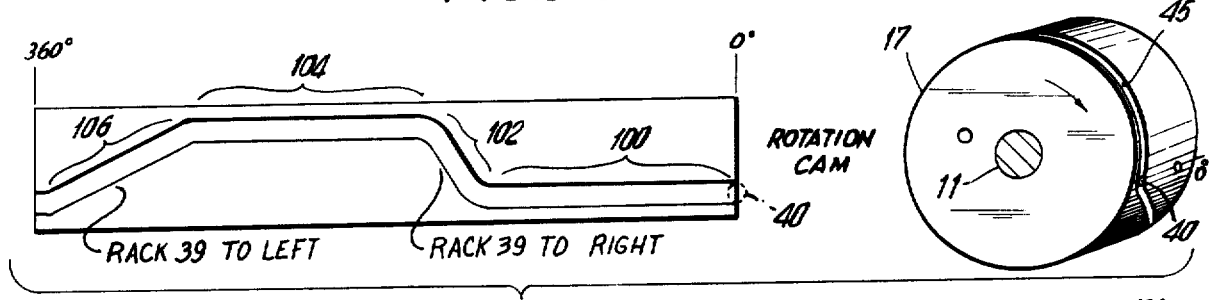

Concurrently with the foregoing movement of arm 55, by operation of the elements discussed in connection with FIG. 7, reagent arm 31 is lowered from its first position shown in FIG. 2 by the advance of follower 28 of cam 15 at location 82 as shown in FIG. 9(a), to its "second position" as shown in FIG. 2. With reference to FIG. 2, reagent arm 31 remains in the second position while follower 28 is at location 84 as shown in FIG. 9(a) and reagent arm 31 is raised back to its first position shown in FIG. 2. Follower 28 and hence reagent arm 31 is in a raised position, with follower 28 at location 88 shown in FIG. 9(a) while as shown in FIG. 9(b) cam 17 advances follower 40 from its dwell location 100 to location 102 which with reference to FIG. 2, causes gear rack 39 to move to the right and rotate shaft 30 and arm 31 counter clockwise to its third position shown in FIG. 2 by rotating gear 38 and shaft 30 in a counter clockwise direction. Follower 28 of cam 15 at this time advances through location 90 as shown in FIG. 9(a) and reagent arm 31 is lowered to its "fourth position" as shown in FIG. 2 and remains in this position through dwell location 92 of FIG. 9(a) and is raised as follower 28 of cam 15 advances through location 94 of FIG. 9(a). With reagent arm 31 in a raised position as indicated at location 96 follower 40 of cam 17 advances from dwell location 104 to location 106, as shown in FIG. 9(b) which causes rack 39 to be moved to the left, rotating gear 38 and shaft 30 in a clock-wise direction to return reagent arm 31 to its first position as shown in FIG. 2.

Figure 5:
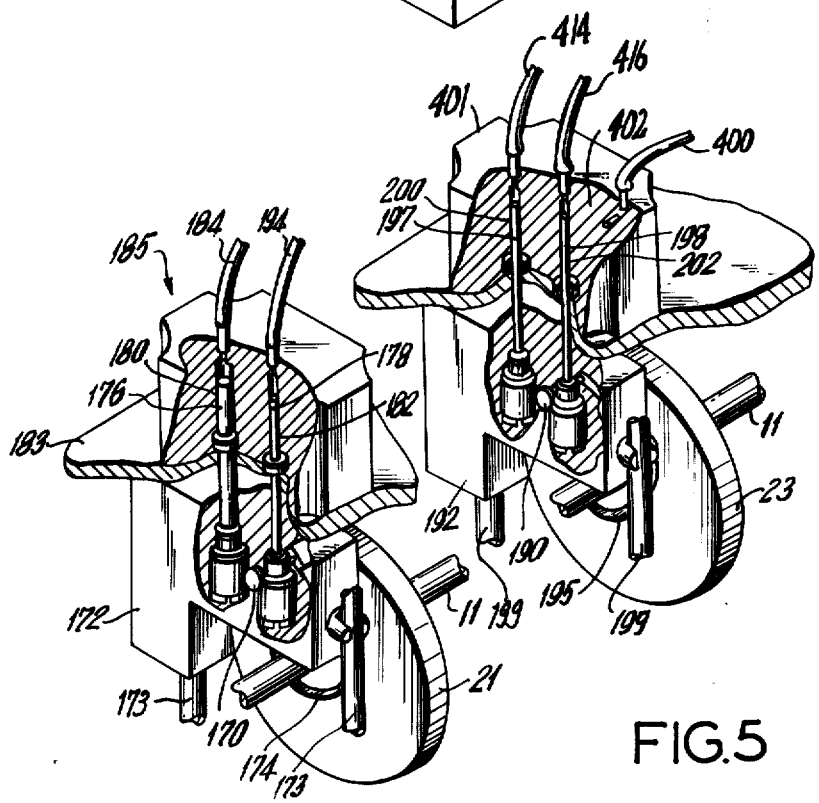
FIG. 5 shows a perspective view of the syringe pump portion of the apparatus of the present invention for picking up and dispensing precise liquid volumes.
Figure 9C:
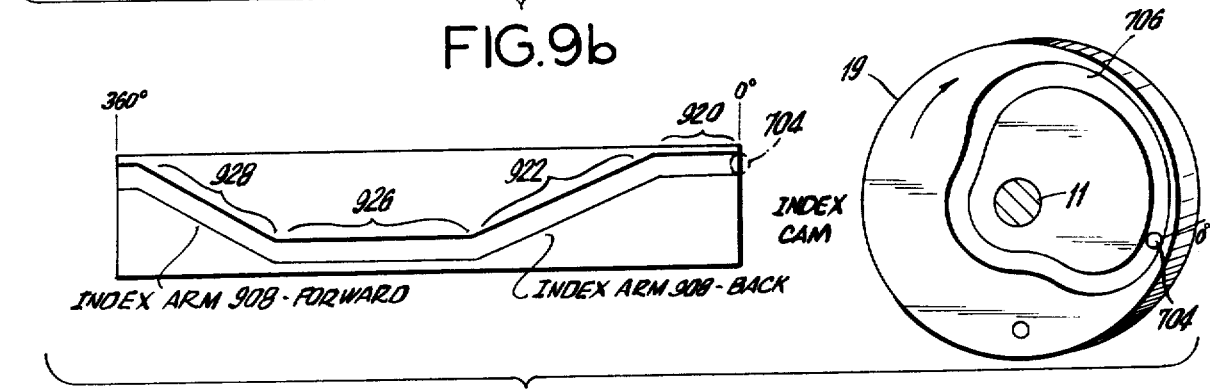
Figure 9D:
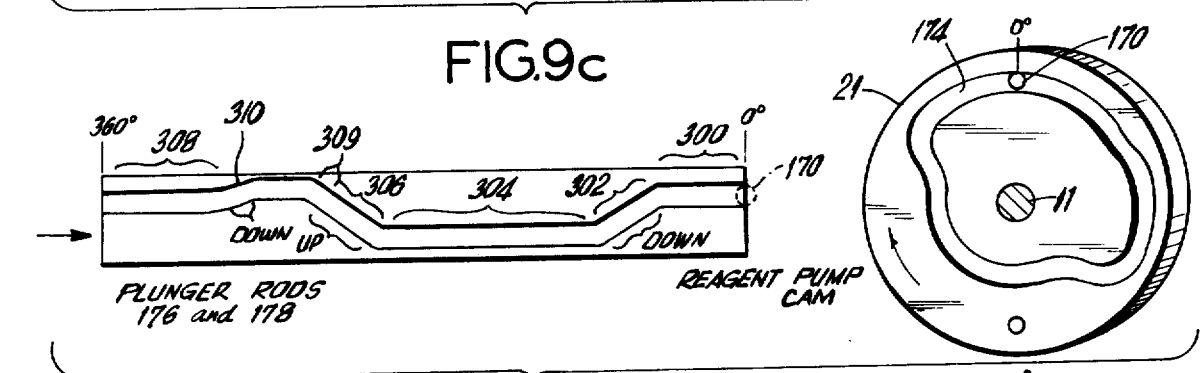

With reference to FIG. 2 it can be seen that a cam 21 is additionally fixed mounted on shaft 11 and engaged to motor 3 by way of gear 7 and completes a revolution with cams 15 and 17 and cams 47 and 61. Cam 21 actuates syringe pumps 180 and 182 to pick up and dispense reagents in coordination with the previously described movement of reagent arm 31. As shown in FIG. 2 and FIG. 5 slide 172 is slidably mounted on rods 173 attached to base plate 175 and is provided with a follower 170 which is engaged in groove 174 of cam 21. Upon rotation of cam 21, slide 172, and plunger rods 176 and 178 attached thereto move vertically up and down. The plunger rods 176 and 178 thus move in and out of the barrels of syringe pumps 180 and 182 which are formed in housing 185 which is mounted on plate 183 and connected to probes 35 and 34. Syringe pump 180 is connected to probe 35 via conduits 184, solenoid valve 188 and conduit 186, and syringe pump 182 is connected to probe 34 via conduit 194, solenoid valve 190 and conduit 192. Solenoid valves 188 and 190 are deenergized and during regular operation involving loading of all the cavity rows of disc 67 and are actuated under particular circumstances described hereinbelow. Thus the rotation of cam 21 and the resultant movement of plunger rods 176 and 178 in syringe pumps 180 and 182 enables the intake of fluids into probes 34 and 35 from the liquid containing compartments of reagent reservoir 50 and the dispensing of the picked up liquid reagent from probes 34 and 35. The volume of the barrels of pump 180 and 182 and the travel of plunger rods 176 and 178 are designed and selected to provide a predetermined volume of picked up and dispensed liquid. The intake of reagent into probes 34 and 35 is coordinated with the position of reagent arm 31 by the arrangement and operation of cam 21 of shaft 11 as shown in the diagram of FIG. 9(c). With reference to FIG. 9(c), cam 21 is shown in the indexed position at which time arm 31 is in its first position as indicated in FIG. 2 above reagent reservoir 50. While reagent arm 31 in its first position, follower 170 of cam 21 advances through dwell location 300 as shown in FIG. 9(c) and plunger rods 176 and 178 of pumps 180 and 182 remain stationary. When reagent arm 31 is lowered to its second position shown in FIG. 2, with probes 34 and 35 immersed in the liquids in the compartments reagent reservoir 50, follower 170 of cam 21 advances through location 302 as shown in FIG. 9(c) and piston rods 176 and 178 move down in pumps 180 and 182 a fixed distance and precise amounts of liquid from the compartments of reagent reservoir 50 are drawn into reagent probes 34 and 35. While reagent arm 31 is being moved to its third position follower 170 of cam 21 advances through dwell location 304 shown in FIG. 9(c) and piston rods 176 and 178 remain stationary holding the picked up liquid in probes 34 and 35. With reagent arm 31 moved to its fourth position with probes 34 and 35 in cavities of disc 67, follower 170 of cam 21 advances through location 306 of FIG. 9(d) and piston rods 176 and 178 are moved upward a fixed distance and precise volumes of picked-up liquid reagents are dispensed from probes 34 and 35 into cavities of disc 67. After dispensing of liquid reagent from probes 34 and 35, follower 70 of cam 21 advances to dwell location 308 shown in FIG. 9(d) and piston rods 176 and 178 of pumps 180 and 182 are returned to their initial position. The relatively slight upward movement of piston rods 176 and 178, indicated at 309 represents an over-travel of the piston rods 176 and 178 and compensates for the compression of air in conduits 186 and 192 in the course of the upward dispensing of piston rods 176 and 178 to ensure that all of the picked-up reagents are dispensed from probes 34 and 35. The piston rods 176 and 178 are returned to these initial positions by the downward movement indicated at 310.

Figure 8:
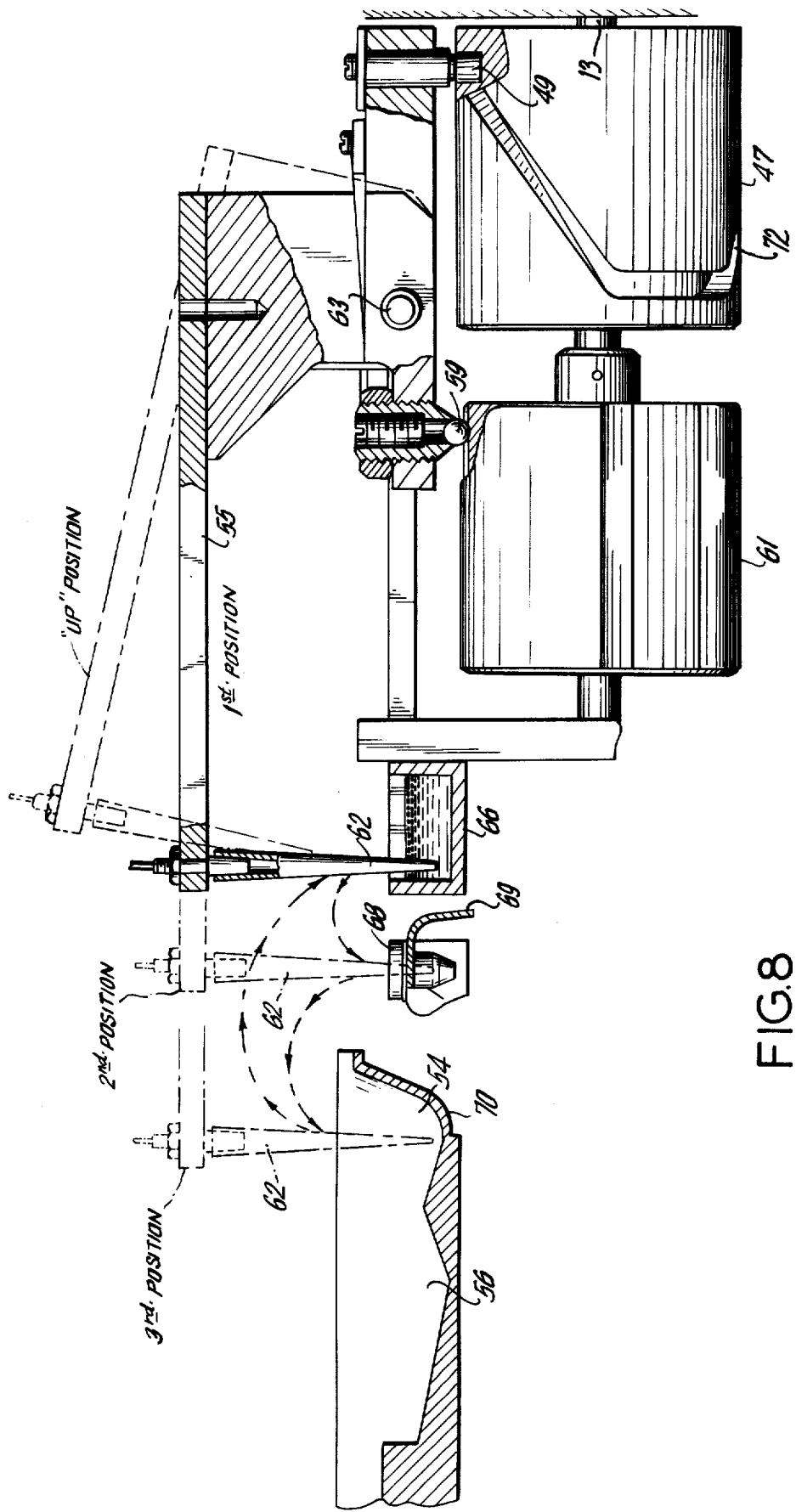
FIG. 8 shows the movement of the sample arm of the apparatus of FIG. 2 during operation.
Figure 9E:
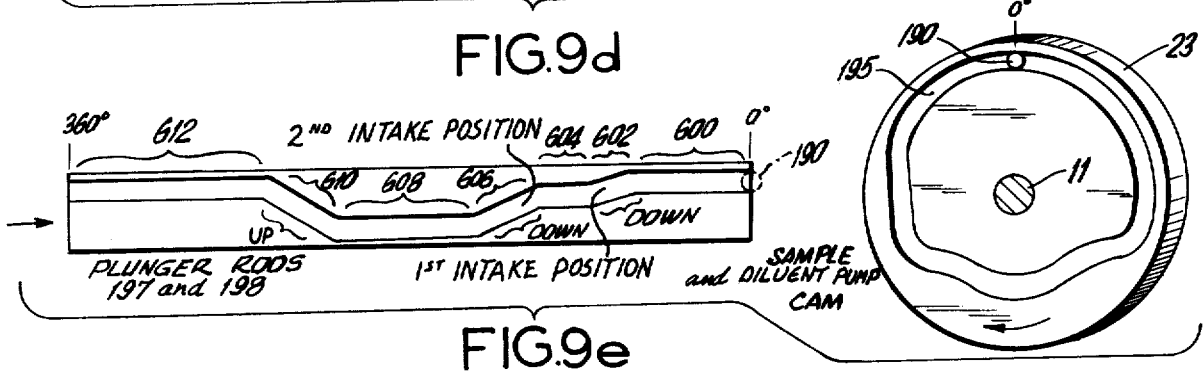

With further reference to FIGS. 2 and 5, a cam 23 is also fixedly mounted on shaft 11 and engaged to motor 3 by way of gear 7 and completes one revolution with cam 15, 17, 47, 61 and 21. Cam 23 actuates syringe pumps 200 and 202 to pick-up and dispense sample and diluent in coordination with the previously described movement of sample arm 55. As shown in FIG. 2 and 5 a slide 192, similar to slide 172 is mounted in the same manner as slide 172 on rods 199 affixed to base plate 175 and is similarly provided with a follower 190 which is engaged in groove 195 of cam 23. Upon rotation of cam 23 slide 192, and plunger rods 197 and 198 attached thereto move vertically up and down similarly as plunger rods 176 and 178 of pumps 180 and 182 but in a different sequence as determined by groove 195 of cam 23. The plunger rods 197 and 198 move in and out of the barrels of syringe pumps 200 and 202 which are connected to sample probe 62 of sample arm 55. Sample probe 62 is connected by conduit 400 to a T-connection 402, more clearly indicated in FIG. 13, located in pump housing 401 which communicates with solenoid valves 404 and 406 as also shown in FIG. 13. Solenoid valves 404 and 406 communicate with diluent reservoir 408 by way of conduits 410 and 412 and with pumps 200 and 202 by way of conduits 414 and 416. The operation of pumps 200 and 202 will be more clearly understood with reference to FIGS. 9(e) and 13. With cam 23 in the indexed position shown in FIG. 9(e) sample probe 62, supported on sample arm 55 is in the first position shown in FIGS. 2 and 8, immersed in wash liquid reservoir 66 as illustrated in FIG. 8. At this time probe 62 and conduits 400, 410, 412, 415, 414, 416 and 417 are primed with diluent liquid. As follower 190 of cam 23 advances through dwell location 600, shown in FIG. 9(e), piston rods 197 and 198 of pumps 200 and 202 remain stationary and sample arm 55 is in its first position. As follower 190 of cam 23 advances through location 602, as shown in FIG. 9(e) sample arm 55 is in its second position with probe 62 immersed in sample cup 68, and plunger rods 197 and 198 of syringe pumps 200 and 202 are each lowered the same distance. Syringe pump 200 is the sample-pick up pump, and solenoid valve 404 is adapted to be energized by an electrical signal applied to solenoid coil 607 from the Control Logic Unit as hereinafter described; with solenoid valve 404 energized while plunger rod 197 is being lowered, an increment of sample is drawn into sample probe 62. After advancing through dwell location 604, shown in FIG. 9(e) follower 190 of cam 23 advances through location 606 and plunger rods 197 and 198 of syringe pumps 200 and 202 are lowered and additional distance. Sample arm 55 has remained in its second position and with solenoid valve 404 remaining in the energized condition and additional increment of sample is drawn into sample probe 62. After advancing through dwell location 608 follower 190 of cam 23 advances through location 610 as shown in FIG. 9(e) and plunger rods 197 and 198 of syringe pumps 200 and 202 are raised. Sample arm 55 is in its third position, as shown in FIG. 8, over a cavity of disc 67 during the raising of the plunger rods and the total amount of sample taken into sample probe 62 is dispensed into the cavity.

During the aforedescribed advance of follower 190 cam 23 solenoid valve 406 remains deenergized through locations 600, 602, 604 and 606 shown in FIG. 9(e) and diluent liquid is drawn from diluent reservoir 408 during the lowering of plunger rod 198 of pump 202 at locations 602 and 606 shown in FIG. 9(e). Solenoid valve 406 is energized by the application of an electrical signal from the Control Logic unit, as hereinafter described, while follower 190 is advancing through dwell location 608. Consequently, the raising of plunger rod 198 of pump 202 at location 610 shown in FIG. 9(e) causes diluent to be dispensed from sample probe 62 into disc 67 together with sample, the amount of diluent being determined by the geometry of pump 202. In view of the incremental downward movement of plunger rod 197 of syringe pump 200 it is possible to incrementally control the amount of sample picked-up by sample probe 62. For example, if solenoid valve 404 is deenergized instead of energized during the lowering of plunger rod 197 for cam location 602, pump 200 takes in diluent from reservoir 409 instead of picing up sample and sample will only be picked up at cam location 606. However, upon the raising of plunger rod 197 of pump 200 at cam location 610, the same volume as before will be dispensed by pump 200. Thus, the same total volume of liquid is dispensed each time by sample probe 62. It can be seen that by deenergizing solenoid valve 404 during the lowering of plunger rod 197 for cam location 602, an incremental amount of diluent, instead of sample will be picked up by pump 200. Consequently, by selectively energizing and deenergizing solenoid valve 404 incrementally different amounts of sample can be picked-up and dispensed. By way of example, if cam location 602 causes a pick-up of 15 $\mu$l, and a cam location 606 35 $\mu$l, the amount of sample picked-up by sample probe 62 can be 15 $\mu$l, 35 $\mu$l or 50 $\mu$l depending on the condition of solenoid valve 404.

Figure 6:
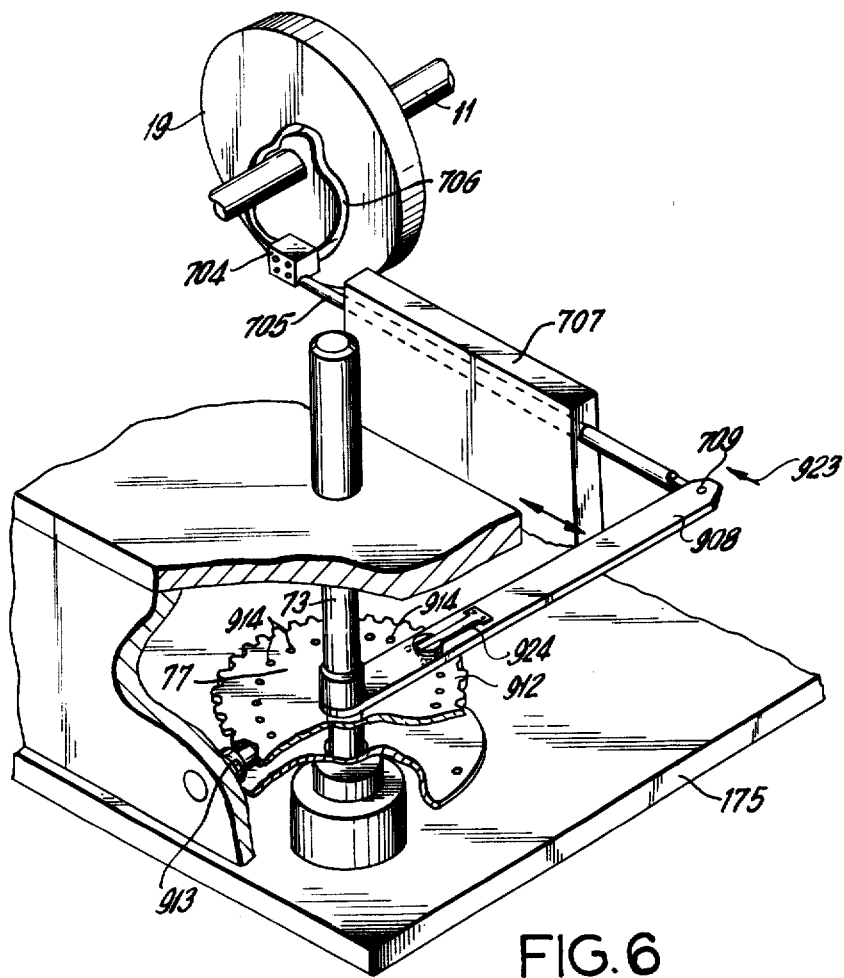
FIG. 6 shows a perspective view of the indexing arrangement of the present invention which functions to advance cavity rows to a loading position.

When sample arm 55 and reagent arm 31 are returned to their first positions shown in FIG. 2, after the dispensing of liquid from probes 34, 35 and 62 into rows of cavities of disc 67 as above described, cam 19 operates to advance sample ring 69 and disc 67 so that the next adjacent sample and cavity row are in position to receive liquid from probes 34, 35 and 62. As shown in FIG. 2 cam 19 is fixedly engaged to shaft 11 which is rotatably driven by motor 3 by way of gear 7 by the operation as above described. With reference to FIGS. 2 and 6 follower 704 of rod 705, slidably engaged in mounting block 707, engages groove 706 of cam 19 and is pivotally connected at 709 to arm 908. Index arm 908 slidably engages shaft 73 at 77 above toothed disc 912 which is fixedly attached to shaft 73. During the picking up and dispensing of liquid in the operation above described, disc 912 is firmly held in a stationary position by a spring-loaded detent member 913.

With reference to FIGS. 2 and 8, while sample arm 55 and reagent arm 31 are moving from their first position follower 704 of cam 19 advances through dwell location 920 and through location 922 as shown in FIG. 9(c) causing index arm 908 to move in the direction indicated at 923 in FIG. 6, causing spring mounted pin 924 to be raised and disengaged from disc 912 and be reengaged in slot 914 of disc 912. Follower 704 of cam 19 advances in dwell location 926 shown in FIG. 9(c) and index arm 908 remains stationary until reagent arm 31 and sample arm 55 have been raised subsequent to the dispensing of liquid from probes 34, 35 and 62; thereafter follower 704 advances through location 928 shown in FIG. 9(c) causing index arm 908 to return to its initial position at the same time rotating shaft 73 to a position which brings the next row of cavities of disc 67 into the position required to receive liquid from probes 34, 35 and 62 and the above described operation is repeated for the next revolution of cam shafts 11 and 13 until the desired rows of cavities of disc 67 have received reagents and sample.

In instances where it is desired that reagent probe 35 be enabled to pick-up and dispense more than one liquid reagent, reservoir 50, as shown in FIGS. 2 and 3a, is provided with separate compartments 976 and 977 and slidably mounted between brackets 980 and 981 on rods 983 and 985. Reservoir 50 is provided with a follower 950 which engages groove 952 in cam 954 which can be rotated upon actuation of motor 956 by way of gears 959 and 960. With reference to FIG. 11 when cam 954 is rotated by motor 956 follower 950 advances through location 970 and reservoir 50 is moved to the location indicated at 975, with reagent probe 35 over compartment 976, instead of 977. Further rotation of cam 954 causes follower 950 to advance through location 975 shown in FIG. 11 and return reservoir 50 back to its initial position with probe 35 over compartments 977. Motor 956 is actuated by a signal from the Control Logic Unit, as hereinafter described to move reagent reservoir 50 at a time when reagent arm 31 is in a raised position.

In some instances, it is not necessary that all of the rows of cavities of disc 67 be used to receive reagent. Under such circumstances, when the last row of cavities to be filled has received reagent from probes 34 and 35, and before the next row of cavities is advanced to a receiving position, solenoids 193 and 196 of solenoid valves 188 and 190, illustrated schematically in FIG. 13(a) are energized by a signal from the Control Logic Unit, as hereinafter described and are vented to atmosphere so that liquid is neither picked-up and dispensed from probes 34 and 35 so long as solenoids 193 and 196 remain energized. Likewise, when the last row of cavities to receive sample liquid has received sample liquid from sample probe 61, solenoid valves 404 and 406 thereafter remain deenergized and pumps 200 and 202 thereafter pick-up diluent liquid and discharge diluent liquid back into reservoir 409 and can be seen from FIG. 13.

The Control Logic Unit shown in FIG. 2 is shown schematically in more detail in FIG. 14. The Control Logic Unit receives input electrical signals by way of optical switches which are synchronized with the mechanical cycle of the apparatus hereinabove described and the Control Logic Unit provides in response to the input signals, various output electrical signals for driving motors 3 and 956, and for selectively energizing the solenois valves 188, 190, 404 and 406. With reference to FIGS. 2 and 14, upon actuation of start switch 1, conventional motor control unit 2015 supplies power to rotate drive motor 3 which provides the mechanical cycle previously described for picking up and dispensing reagents and sample. The shaft 11 has rotated a predetermined amount, e.g. 31° for the particular apparatus described herein, optical switch 2050 is actuated by the passage of an opening 2053 of timing disc 2057 mounted on shaft 11. An electrical signal is thus received for each revolution of cam shaft 11 by the Control Logic Unit via connector 2060 which actuates oscillator 2070 through oscillator control unit 2075. Oscillator 2070 provides clock signals corresponding to degrees of rotation of cam shaft 11 via an appropriate divide unit 2090 to a conventional counter 2080. The output of counter 2080 is applied to a decoder unit 2095 which provides output pulses corresponding to a particular degrees of rotation of cam shaft 11. The decoder output pulses are related to positions of cams 21 and 23 as shown in FIG. 9(a) and 9(b) in order to provide signals to solenoid coils 193, 195, 607, 609 for energizing valves 188, 190, 404 and 406 in the manner hereinabove described in conjunction with FIGS. 12 and 13. The signals for solenoids 607 and 609, which control the pick-up and dispensing of sample and diluent are applied from "AND" gates 3000, 3010, 3020, and 3030, these gates receiving inputs from decoder 2095 and a sample volume selector switch 3030. Depending on the position of selector switch 3030, solenoid coil 607 of sample pump 404 will be energized for different intervals during the rotation of cam 23. With reference to FIG. 14, if selector switch 3040 is in position (a) amplifier 3040 will provide a signal to solenoid coil 607 and energize solenoid valve 404 during the 1st Intake position of cam 23 shown in FIG. 9(e). Position (b) of selector switch 3040 will cause solenoid valves 404 to be energized during the 2nd Intake position and position (c) will cause valve 404 to be energized during both the 1st Intake and 2nd Intake positions. At a rotation 359° a signal from decoder 2095 causes oscillator 2070 to be turned off.

In instances where not all of the cavity rows of a disc 67 are to receive reagent and sample, i.e. less than all of a typical 36 row disc shown in FIG. 4(a) this number is set into binary coded decimal switch 4000. An output of BCD switch 4000 is applied to a BCD "down" counter 4010 which is set by actuation of start switch 1 and counts with a signal received for each revolution of cam shaft 11 from optical switch 2050. When actuated by slot 2053 of disc 2057. When counter 4010 has counted down to "0", zero detector unit 4020 deactuates amplifier 3040 thereby deenergizing solenoid coil 607 and solenoid valve 404 so that the pick-up of sample is discontinued.

The output of BCD switch 4000, corresponding to the number of cavity rows to be filled is also applied to comparator unit 4030. Comparator 4030 also receives the output from BCD "up" counter 4040 which also receives a cam shaft revolution signal from switch 2050 and counts up in synchromium with the down count of BCD counter 4010. However, the counting of BCD counter 4040 is required to be retarded by a number corresponding to the rows of cavities between the dispense positions of sample arm 55 and reagent arm 31, e.g. 12 in the particular apparatus described herein. This is accomplished by "OR" gate arrangements 4050, 4060 and 4070 and detector 4080. Upon receiving a pre-set signal via OR gate 4070, "twelve" is pre-set in BCD counter 4040. After 24 "revolution" signals are applied from optical switch 2050 to BCD counter 4040, "thirty six" is detected by detector 4080 and BCD counter 4040 is reset to "zero" via OR gates 4060 and 4070. When the counts from BCD counters 4000 and 4040 are the same, indicating that the last desired cavity row has received reagents comparator 4030 actuates gage 3050 and solenoid coils 193 and 195 solenoid valves 188 and 190 are thereafter energized during their usual intake interval and pumps 180 and 182 are vented to the atmosphere during this interval and no longer pick up or dispnese reagents.

In some situations it is desired that reagent probe 34 pick up a different reagent for a predetermined cavity row of disc 67. In such a case, the different reagent is placed in compartment 976 of reagent reservoir 50 shown in FIG. 3a, and when the predetermined cavity row is in the loading position for reagent probe 34 reservoir 50 is displaced so that compartment 976 will be beneath probe 34 in the pick-up position for probe 34. This is accomplished by setting the number of the cavity rows of interest in BCD switch 5000 and applying the output to comparator unit 5010. Comparator 5010 also receives an input from BCD up counter 4040. When the count of up counter 4040 corresponds to the number of the cavity row selected to receive different reagent, the output of comparator 5010 actuates motor control unit to cause motor 956 to rotate through one revolution driving cam 954 in the manner previously described in conjunction with FIG. 9. In the course of this revolution reagent reservoir 50 is moved by the action of cam 954 to place compartment 976 under probe 34 during "intake", and return reservoir 50 to its original position after intake. Optical switch 960 actuated by slot 963 in disc 965 positioned to provide an additional electrical signal to motor control unit 5020 to stop motor 956 when compartment 976 of reservoir 50 has been moved under probe 34 by the action of cam 954. Motor 954 remains "stopped" until the count of counter 4040 corresponds to a cavity which is not to receive a "different" reagent at which time motor 954 is caused to rotate by motor control unit 5020.

When the first row of cavities to receive reagent and sample has advanced around to its initial position, optical switch 990 is actuated by slot 992 in disc 38 attached to shaft 73 and a signal is applied to motor control unit 2015 in the Control Logic Unit via connector 994 to stop drive motor 3.

The relationship of electrical signals utilized in the Control Logic of FIG. 14 are shown in the timing diagram of FIG. 15(a), (b) and (c).

FIG. 15(a) is directed to loading of all 36 rows of a 36 row disc as shown in FIG. 3(a) with a separation of 12 rows between the reagent and sample dispense positions as shown in FIG. 3(a). FIG. 15(a) also is directed to a situation where reagent reservoir 50 is to be shifted to provide a different reagent for cavity rows 1 and 2.

FIG. 15(b) is directed to a situation where only 6 of 36 rows are to receive reagent and sample and FIG. 15(c) represents a single pick-up and dispense cycle for one cavity row.

What is claimed is:

1. Apparatus for loading liquid materials into a rotatable disc having a plurality of cavities adapted to contain liquid and arranged in a plurality of radially aligned rows said apparatus comprising:

i. a first horizontally disposed cam shaft,
  ii. a second horizontally disposed cam shaft arranged parallel to and horizontally separated from said first cam shaft,
  iii. electrically actuatable motor means engaged to said first and second cam shafts,
  iv. a first vertically disposed shaft arranged at a position substantially in-line with the axis of rotation of said second cam shaft and spaced adjacent from said first cam shaft, said first vertically disposed shaft being rotatably moveable about its vertical axis,
  v. a disc member removeably affixed to said vertical shaft and rotatable therewith, said disc member having a plurality of cavities adapted to contain liquid, said cavities being arranged in a plurality of equi-spaced radial rows,
  vi. reservoir means adapted to contain liquid reagent positioned adjacent said disc member,
  vii. an annular ring member fixedly positioned with respect to and surrounding said disc member, said ring member having a plurality of receptacles adapted to contain serum, said receptacles being in radial alignment with said radial rows of said disc member,
  viii. a second vertically disposed shaft arranged adjacent said first vertically disposed shaft, said second vertically disposed shaft being reciprocally rotatably moveable about its vertical axis and being vertically moveable up and down,
  ix. a first probe supporting arm fixedly attached to said second vertically disposed shaft, said first probe supporting arm being arranged such that a probe supported thereon can be moved from a position above said reagent liquid reservoir to a position above an initial selected radial row of said disc member and back to a position above said liquid reagent reservoir upon reciprocal rotatable movement of said second vertically disposed shaft,
  x. a first cam mounted on said first cam shaft and engaged to said second vertically disposed shaft to lower and raise said shaft and said first probe supporting arm when the probe supported by said arm is positioned over said reagent reservoir to cause said probe, when lowered, to be immersed in liquid reagent in said reagen reservoir and to subsequently lower and raise said first probe supporting arm when the probe supported by said arm is positioned over said initial selected radial row of said disc member to cause said probe, when lowered, to be within a cavity of said selected radial row,
  xi. a second cam member mounted on said first cam shaft and engaged to said second vertically disposed shaft to reciprocally rotate said second vertically disposed shaft and said first probe supporting arm from an initial position in which the probe supported by said arm is above said liquid reagent reservoir to a second position in which said probe is above said initial selected radial row of said disc member and back to its said initial position,
  xii. a horizontally, moveably mounted block arranged above said second cam shaft,
  xiii. a second probe supporting arm pivotally mounted on said horizontally moveable block and arranged to be rotatably moveable up and down in a vertical plane,
  xiv. a rinse liquid containing reservoir arranged adjacent said second cam shaft,
  xv. a third cam mounted on said second cam shaft and engaged to said horizontally moveable block to move said second probe supporting arm such that the probe supported thereby is moved in sequence from (a) an initial position in said rinse liquid reservoir to (b) a position within a said receptacle of said ring member to (c) a position within a cavity of a radial row of said disc member and (d) back to its initial position within said rinse liquid reservoir,
  xvi. a fourth cam mounted on said second cam shaft and engaged to said pivotally mounted second probe supporting arm to move said second probe supporting arm such that the probe supported thereby is raised during sequence (a) of (xv) above, lowered during sequence (b) of (xv) above, raised subsequent to sequence (b) lowered during sequence (c) of (xv) above raised subsequent to sequence (c) of (xv) above and lowered during sequence (d) of (xv) above,
  xvii. first syringe pump means arranged adjacent said first cam shaft and communicating with a said probe supported by said first probe supporting arm,
  xviii. fifth cam means mounted on said first cam shaft and engaged to said first syringe pump means to cause relative movement of the syringe of said first syringe pump means such that liquid reagent is drawn into a said probe of said first probe supporting arm when said probe is immersed in liquid reagent in said reagent reservoir and dispensed from said probe when said probe is within a cavity of a selected radial row of said disc member,
  xix. second syringe pump means arranged adjacent said first cam shaft and communicating with said probe supported by said second probe supporting arm,
  xx. sixth cam means mounted on said first cam shaft and engaged to said second syringe pump means to cause relative motion of the syringe of said second syringe pump means such that serum is drawn into said probe of said second probe supporting arm when said probe is within a said receptacle of said ring member and dispensed from said probe when said probe is within a cavity of a radial row of said disc member,
  xxi. seventh cam means mounted on said first cam shaft and engaged to said first vertically disposed shaft to rotate said shaft by an increment corresponding to one radial row of cavities of said disc member subsequent to the dispensing of liquid from the probes supported by said first and second probe supporting arms.

2. Apparatus in accordance with claim 1 wherein electrically operable solenoid valves are arranged in communication with said first and second syringe pumps to selectively control the intake and dispensing of liquid from said first and second syringe pumps in response to electrical signals provided by electrical switch means synchronized with the rotation of said first cam shaft.

3. Apparatus in accordance with claim 1 wherein third syringe pump means are engaged to said sixth cam means and in communication with said probe of said second probe supporting arm and a diluent liquid to provide an intake and dispensing of diluent liquid through said probe.

* * * * *